(12) United States Patent
Sadanand (10) Patent No.: US 8,777,844 B1
(45) Date of Patent: Jul. 15, 2014

(54) MODIFIABLE ENDOSCOPE DEVICE

(76) Inventor: Siddharth Sadanand, Toronto (CA)

( * ) Notice: Subject to any disclaimer, the term of this patent is extended or adjusted under 35 U.S.C. 154(b) by 58 days.

(21) Appl. No.: 13/466,687

(22) Filed: May 8, 2012

(51) Int. Cl.
*A61B 1/00* (2006.01)
*A61B 1/005* (2006.01)
*A61B 1/008* (2006.01)
*A61B 1/04* (2006.01)

(52) U.S. Cl.
CPC .......... *A61B 1/0055* (2013.01); *A61B 1/00149* (2013.01); *A61B 1/0056* (2013.01); *A61B 1/0057* (2013.01); *A61B 1/008* (2013.01); *A61B 1/00071* (2013.01); *A61B 1/00135* (2013.01)
USPC ............................. 600/141; 600/149; 600/114

(58) Field of Classification Search
CPC .......... A61B 1/00071; A61B 1/00135; A61B 1/00149; A61B 1/0055; A61B 1/0056; A61B 1/0057; A61B 1/008
USPC ......... 600/105, 129, 139–142, 153, 102, 106, 600/114, 117, 149
See application file for complete search history.

(56) References Cited

U.S. PATENT DOCUMENTS

| 1,747,407 | A | * | 2/1930 | Wappler | 600/153 |
| 5,609,565 | A | * | 3/1997 | Nakamura | 600/229 |
| 2005/0107663 | A1 | * | 5/2005 | Saadat et al. | 600/104 |

* cited by examiner

*Primary Examiner* — Alireza Nia
(74) *Attorney, Agent, or Firm* — Blakely Sokoloff Taylor & Zafman LLP (57) ABSTRACT

An apparatus including an outer articulated tube member, the outer articulated tube member having a first tubular section and a second tubular section. The apparatus further including an inner articulated tube member positioned within the outer articulated tube member, the inner articulated tube member having a first tubular section and a second tubular section. The first tubular section and the second tubular section of at least one of the outer articulated tube member and the inner articulated tube member are movable with respect to one another in a first configuration and fixed with respect to one another in a second configuration.

13 Claims, 12 Drawing Sheets

MODIFIABLE ENDOSCOPE DEVICE

BACKGROUND

1. Field

A modifiable elongated device, more specifically, an endoscope capable of transitioning between a rigid or fixed configuration and a modifiable or flexible configuration to change a shape of the device.

2. Background

An endoscope is a medical instrument used to examine and perform various interventions within the interior of a hollow organ or cavity of the body, or in the case of a neuroendoscope, the central nervous system. Endoscopes generally include a tube that can be advanced through the body to the region of interest, a light delivery system (e.g., an optical fiber system) to illuminate the organ or object under inspection, a lens system for transmitting the image to the viewer, an eyepiece and one or more channels to allow entry of medical instruments or manipulators through the endoscope body.

Endoscopes can be flexible or rigid depending on the desired use. For example an endoscope having a flexible body can be advanced through the winding intestinal tract to reach a target region. The flexible body, however, remains flexible through the surgical procedure and has a fixed length. It can therefore be difficult to control the device and reach a target region that may be farther away then anticipated. In addition, since the body is flexible, it must be advanced through an open passageway. Flexible endoscopes are therefore not suitable for surgical procedures that require advancement of the device through body tissues. In such cases, a rigid endoscope is used.

A rigid endoscope, for example a neuroendoscope, typically has a rigid tube that can be advanced through the skull and brain directly to the brain region of interest. In particular, the region of interest is determined in advance and then a small hole is formed in the skull. The neuroendoscope is then inserted through the hole directly to the region of interest. Since the neuroendoscope is inserted through brain matter, the rigidity is important to ensure that it does not deviate from the desired course and unnecessarily compromise the surrounding brain matter.

The rigidity of the neuroendoscope, however, also has several disadvantages. In particular, the surgeon is working in an extremely narrow field of view so it may be difficult to view and maneuver around a region of interest that is larger than expected, for example, a large tumor. In addition, it is not uncommon for blood vessels to get nicked while the tube is being advanced through the brain. When this happens, the surgeon may see a sudden spurt or gush of blood but the surgeon may not know where the blood is coming from. The endoscope can be moved slightly from the path to the region of interest to try and identify the damaged vessel, but movement is extremely limited. In particular, since a diameter of the hole formed in the skull is typically only around 1 centimeter (cm), the angle within which the endoscope can move is limited. Moreover, movement of the neuroendoscope in different directions slices the brain matter. Thus, in trying to chase a bleeding blood vessel or trying to obtain a different view of a large tumor, brain matter is unnecessarily compromised. In addition, due to the rigidity of the neuroendoscope, the region of interest can only be approached at a fixed angle and some targets may be inaccessible at this angle because of where they are located.

In addition, endoscopes typically have a fixed length therefore a target region that is beyond the length of the selected endoscope may cause further surgical complications.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

In this section we shall explain several preferred embodiments with reference to the appended drawings. Whenever the shapes, relative positions and other aspects of the parts described in the embodiments are not clearly defined, the scope of the embodiments is not limited only to the parts shown, which are meant merely for the purpose of illustration. Also, while numerous details are set forth, it is understood that some embodiments may be practiced without these details. In other instances, well-known structures and techniques have not been shown in detail so as not to obscure the understanding of this description.

The following embodiments are directed to a modifiable elongated device that is both modifiable or flexible and fixed or rigid, and can be modified between the flexible and rigid configurations during use. Representatively, in one embodiment, the elongated device may be an endoscope having tubular sections which, in one configuration, can move with respect to one another to allow for bending of the device, and in another configuration, are fixed with respect to one another so that the device is maintained in the desired position. The ability of the device to transition between a modifiable or flexible configuration and a fixed or rigid configuration allows the device to be advanced to a desired location and bend to reach a different location. For example, in the case of a neuroendoscope, the device can be straightened and placed in the rigid or fixed configuration so that it can be advanced through the desired body region to the target area. If, while the device is being advanced or once it has reached the target area, it is determined that a peripheral region outside the target area needs to be examined, the device can transition to the movable or flexible configuration and the tubular sections can be bent with respect to one another so that the peripheral area can be viewed without having to remove and reinsert the endoscope within the patient and without having to damage the brain tissue along the entire length of the endoscope. In addition, the elongated device may include a length that is modifiable during a procedure so that a target area that is farther than anticipated can be reached without having to remove the device.

The term "flexible" as used herein is intended to refer to a modifiable or movable configuration of the device in which one of the tubular sections is capable of moving or bending with respect to another tubular section. This is in contrast to "rigid" in which the tubular sections are in a fixed configuration with respect to one another and do not bend or flex with respect to one another.

Figure 1:
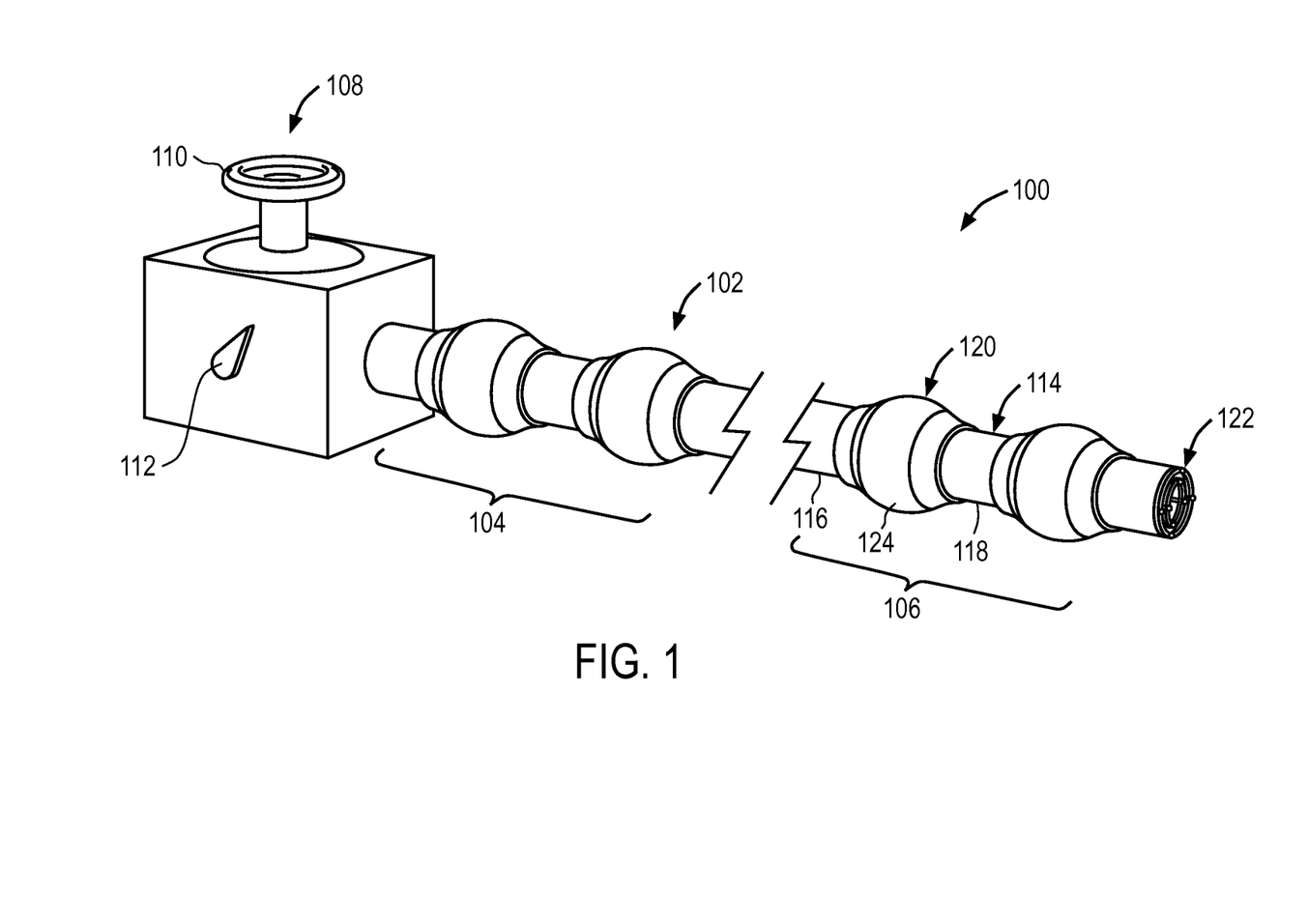
FIG. 1 illustrates a perspective view of one embodiment of a modifiable elongated device.

FIG. 1 illustrates a perspective view of one embodiment of a modifiable elongated device. Elongated device 100 may include an elongated body portion 102 having a proximal portion 104 and a distal portion 106. In embodiments where elongated device 100 is an endoscope, distal portion 106 is inserted into the body of the patient while proximal portion 104 remains external to the patient. Proximal portion 104 may be connected to a control member 108 for controlling the operation of elongated body portion 102 during a procedure. In the illustrated embodiment, control member 108 is a motorized or mechanically operated control mechanism that includes joystick 110 for bending and straightening the elongated body portion 102 and lever 112 for extending and retracting the elongated body portion 102. It is contemplated, however, that control member 108 may be any type of mechanism capable of controlling the operation of elongated body portion 102, for example a forceps type control mechanism.

Elongated body portion 102 may be made of one or more articulated tube members that allow elongated body portion 102 to bend or flex in one configuration and remain in a fixed or rigid position in another configuration. Representatively, in one embodiment, elongated body portion 102 may be made of an outer articulated tube member 114 and an inner articulated tube member 214 (see FIG. 2). Inner articulated tube member 214 may be concentrically inward to outer articulated tube member 114.

Outer articulated tube member 114 may include tubular sections 116, 118 that are joined to one another at their ends by joint member 120. Tubular section 118 may be a distal tubular section and tubular section 116 may be proximal to tubular section 118 and therefore considered a proximal tubular section.

Joint member 120 may be any type of joining mechanism capable of joining tubular sections 116, 118 together and allowing them to move with respect to one another in a first configuration and remain fixed or locked with respect to one another in a second configuration. The various components of joint member 120 may be protected by cover member 124. Cover member 124 may be, for example, a flexible elastomeric casing that surrounds the components of joint member 120. Although two tubular sections 116, 118 connected by joint member 120 are labeled in FIG. 1, each of the illustrated tubular sections and joint members may be substantially the same and outer articulated tube member 114 may have any number of tubular sections and joint members necessary to achieve a desired device length and maneuverability.

Elongated device 100 may further include guide member 122 positioned at the end of distal portion 106 to help guide and control movement of elongated device 100 to the target area. Guide member 122 will be discussed in more detail in reference to FIGS. 5-7

Each of the components of elongated device 100 (e.g., tubular sections, joint member, etc.) may be made of any material sufficiently strong to perform the desired procedure while still being safe for use within the body. Representatively, elongated device 100 may be made of a metal, a polymer, a ceramic or a composite material that may be a combination of any of these materials. For example, in some embodiments, elongated device 100 is made of titanium and can include a coating over the titanium that extends the longevity of the device. A representative coating may include titanium nitride (TiN). Additionally, a graphite coating may be applied to any contact surfaces of the components so that they may move smoothly relative to each other.

In one embodiment, the overall length of elongated device 100 may be anywhere from 20 centimeters (cm) to 30 cm, for example, about 25 cm. Elongated device may have any number of tubular sections 116, 118 and joint members 120, for example from about 20 to about 25 sections with a joint member in between. In addition, a maximum diameter of elongated device 100 may be from about 5 millimeters (mm) to about 10 mm, for example about 7 mm. Although specific dimensions are disclosed, it is contemplated that elongated device 100 may have any dimensions suitable for the desired application.

Figure 2:
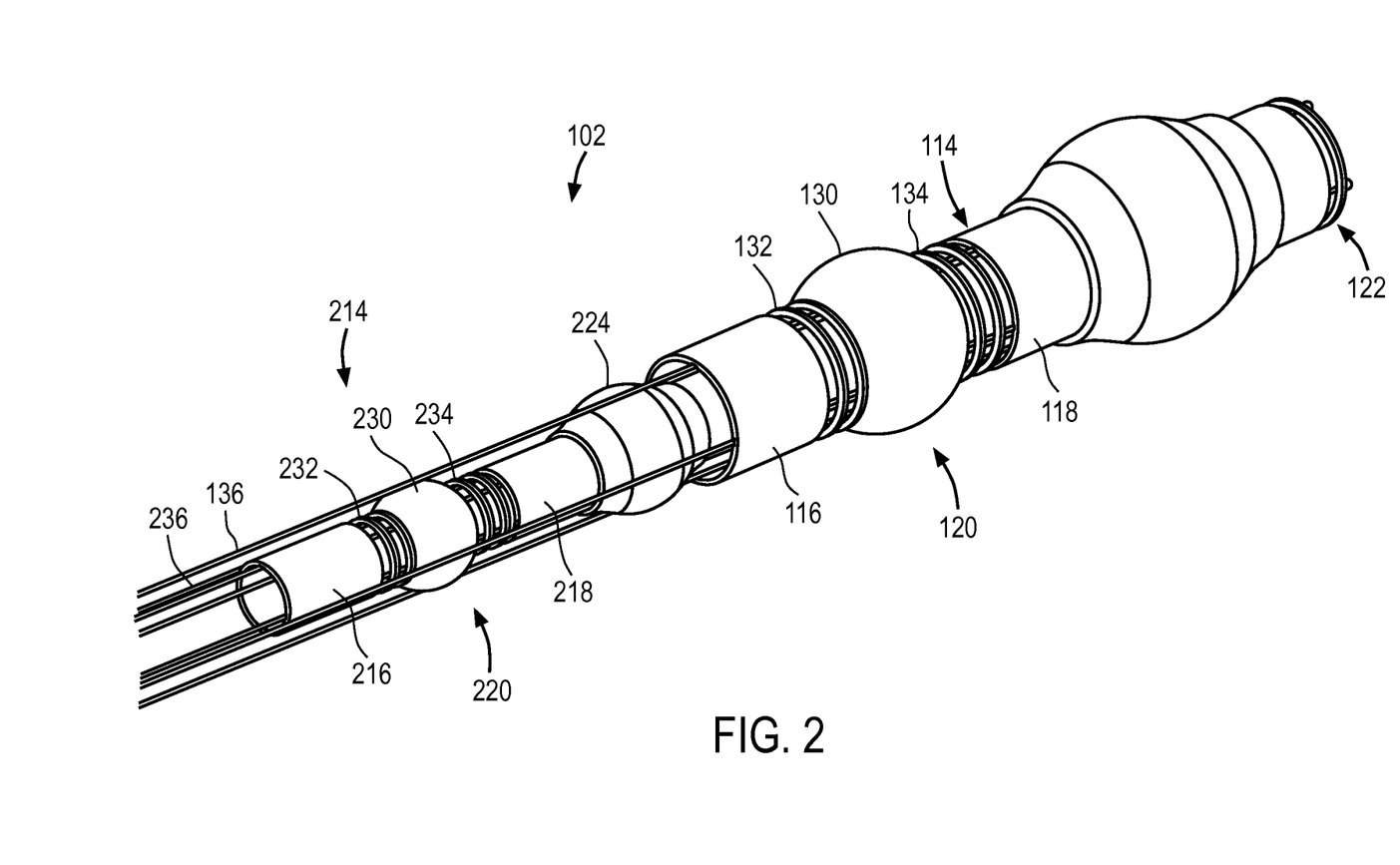
FIG. 2 illustrates a rear perspective partial cutaway view of one embodiment of the modifiable elongated device illustrated in FIG. 1.

FIG. 2 illustrates a rear perspective partial cutaway view of one embodiment of the modifiable elongated device illustrated in FIG. 1. From this view, it can be seen that inner articulated tube member 214 is disposed within outer articulated tube member 114. Inner articulated tube member 214 is substantially similar to outer articulated tube member 114 except that an overall diameter of inner articulated tube member 214 is less than that of outer articulated tube member 114. In one embodiment, inner articulated tube member 214 may include tubular sections 216, 218 that are joined to one another at their ends by joint member 220. Joint member 220 may be any type of joining mechanism capable of joining tubular sections 216, 218 together and allowing them to move with respect to one another in a first configuration and remain fixed or locked with respect to one another in a second configuration. Similar to joint member 120 of outer articulated tube member 114, the various components of joint member 220 may be protected by cover member 224. Cover member 224 may be made of the same or different material as cover member 124 previously discussed in reference to FIG. 1. Although two tubular sections 216, 218 connected by joint member 220 are described in reference to inner articulated tube member 214, it is contemplated that any number of tubular sections and joint members necessary to achieve a desired device length and maneuverability may be included.

As previously discussed, in one configuration, elongated body portion 102 is flexible or modifiable while in another configuration, elongated body portion 102 is rigid or fixed. Each of joint member 120 and joint member 220 shown in FIG. 2 with their respective cover members removed, are therefore joining mechanisms capable of accommodating both configurations. In one embodiment, joint member 120 may be a spring and ball joint that includes ball 130 and spring members 132, 134 positioned between tubular sections 116, 118. In one embodiment, one end of each of spring members 132, 134 is attached to the adjacent tubular section 116 or 118 and the opposite end is free to rotate around ball 130. In this aspect, tubular sections 116, 118 can pivot or articulate around ball 130 to any position within the volume of a cone so that an angle between tubular section 116 and tubular section 118 can be modified. A tension between tubular sections 116, 118 and ball 130 can be modified to either allow or prevent movement of tubular sections 116, 118 with respect to one another. Representatively, in one configuration, tubular sections 116, 118 can be tightened against ball 130 and respective spring members 132, 134 contracted to increase a frictional force between ball 130 and tubular sections 116, 118 to prevent movement of tubular section 116 and tubular section 118 with respect to one another. In another configuration, spring members 132, 134 can be allowed to expand to their resting configuration so that tubular section 116 and tubular section 118 are no longer tightly held against ball 130. In this configuration, tubular sections 116, 118 are free to pivot around ball 130 so that an angle between tubular section 116 and tubular section 118 can be modified.

Tubular sections 116, 118 and spring members 132, 134 can be tightened or loosened around ball 130 using one or more control cables 136 which extend from the proximal end to the distal end of outer articulated tube member 114. Control cables 136 may run along an inner surface of tubular sections 116, 118, spring members 132, 134 and within a cylindrical cavity formed through ball 130. In this aspect, control cables 136 may be positioned between an outer surface of inner articulated tube member 214 and an inner surface of outer articulated tube member 114. Control cables 136 may be connected at a proximal end to control member 108 and a distal end to guide member 122. Using control member 108, each of control cables 136, in this embodiment there are four, can be tightened or loosened to modify a configuration of elongated device 100.

For example, control cables 136 can be pulled in a proximal direction to increase a tension of spring members 132, 134 and in turn increase the frictional forces between ball 130 and tubular sections 116, 118. Due to the high frictional forces between ball 130 and tubular sections 116, 118 in this configuration, tubular sections 116, 118 are maintained in a fixed position with respect to one another. Tubular sections 116, 118 may be fixed in a straight configuration or an angled configuration with respect to one another depending upon the desired use. For example, where elongated device 100 is an endoscope, it may be desirable to maintain outer articulated tube member 114 in a straight configuration so that it can be advanced through the body to a target region. Once at the target region, however, it may be desirable to bend outer articulated tube member 114 to look around. In this aspect, control cables 136 can be loosened using control member 108 so that elongated body portion 102 is in the flexible or movable configuration and one or more of control cables 136 pulled so that elongated body portion 102 can bend.

Loosening of control cables 136 releases the tension on spring members 132, 134 and in turn decreases the frictional forces between tubular sections 116, 118 and ball 130 so that tubular section 116 can move with respect to tubular section 118. In this aspect, outer articulated tube member 114 can be modified from a substantially rigid configuration in which the tubular sections do not move with respect to one another and a flexible or movable configuration in which an angle between each of the tubular sections can be modified. Outer articulated tube member 114 may be transitioned between these two configurations at any point during operation of device 100, e.g., while within the body.

Control cables 136 may also be used to control the direction of movement of tubular sections 116, 118 about ball 130. Representatively, instead of pulling or tightening all of control cables 136, as is the case in the rigid configuration, only the control cable on the side that is desired to bend is pulled while the other cables are loosened. This causes a tension on only one side of outer articulated tube member 114 to increase while the other side is loosened so that bending occurs in the direction of increased tension.

Similar to outer articulated tube member 114, joint member 230 of inner articulated tube member 214 may be a ball and spring joint such that inner articulated tube member 214 may be operated in a manner similar to outer articulated tube member 114. In this aspect, joint member 230 may include ball 230 and spring members 232, 234 positioned between tubular sections 216, 218. Tubular sections 216, 218 can pivot around ball 230 at various angles so that an angle between tubular section 216 and tubular section 218 can be modified. A tension between tubular sections 216, 218 and ball 230 can be modified to either allow or prevent movement of tubular sections 216, 218 with respect to one another using control cables 236. Control cables 236 may run along an inner surface of inner articulated tube member 214 and extend from the proximal end to the distal end of inner articulated tube member 214. Control cables 236 may be connected at a proximal end to control member 108 and a distal end to guide member 122. Using control member 108, each of control cables 236, in this embodiment there are four, can be pulled in a proximal direction to increase a tension of spring members 232, 234 and in turn increase the frictional forces between ball 230 and tubular sections 216, 218. In addition, control cables 236 can be loosened to reduce the frictional forces between ball 230 and tubular sections 216, 218 using control member 108.

Each of outer articulated tube member 114 and inner articulated tube member 214 may be transitioned between the flexible or modifiable and rigid or fixed configurations independently of one another. Representatively, to advance elongated device 100 to a target region, it is desirable for elongated body portion 102 to maintain a rigid or fixed profile. Since inner articulated tube member 214 is concentrically inward from outer articulated tube member 114, only one of members 114, 214 needs to be in the rigid or fixed configuration to prevent bending of elongated body portion 102. For example, outer articulated tube member 114 may be in the rigid or fixed configuration while inner articulated tube member 214 is in the flexible configuration, or vice versa, or both may be in the rigid or fixed configuration.

Elongated body portion 102 may be transitioned from the rigid or fixed configuration to the bendable or modifiable configuration by loosening cables 136 of outer articulated tube member 114 and cables 236 of inner articulated tube member and pulling on the appropriate cable to bend device 100 in the desired direction. The tension may be maintained on the cable selected so that elongated body portion 102 remains fixed in the bent configuration.

Figure 3:
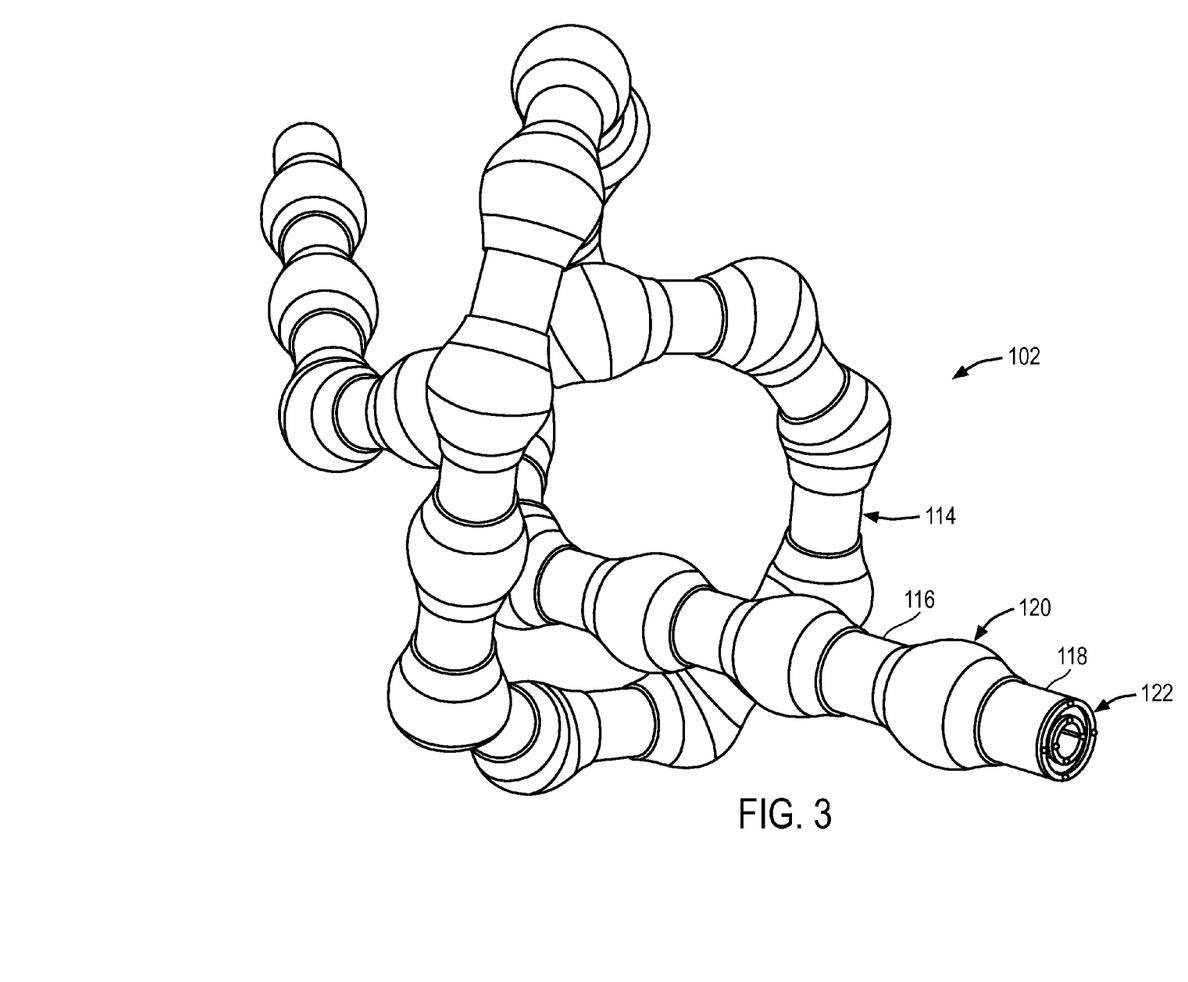
FIG. 3 illustrates a perspective view of one embodiment of a modifiable elongated device bending or curving in different directions.

FIG. 3 illustrates a perspective view of one embodiment of an elongated device bending or curving in multiple different directions. Elongated body portion 102 may include outer articulated tube member 114 having tubular sections 116, 118 that can articulate or move with respect to one another about joint member 120. Although not shown, inner articulated tube member 214 is positioned concentrically inward from outer articulated tube member 112. Elongated body portion 102 includes a plurality of tubular sections 116, 118 and associated joint members 120. As can be seen in FIG. 3, each of tubular sections 116, 118 may articulate about the associated joint member 120 to varying degrees and directions so that elongated body portion 102 can bend or curve in multiple different directions, can invert at points of inflection within its curvature or have a single radius curve. The angle and direction of the curve may be maintained, varied or extended during a procedure by transitioning elongated device between the fixed or rigid configuration and the flexible or modifiable configuration.

Figure 4A:
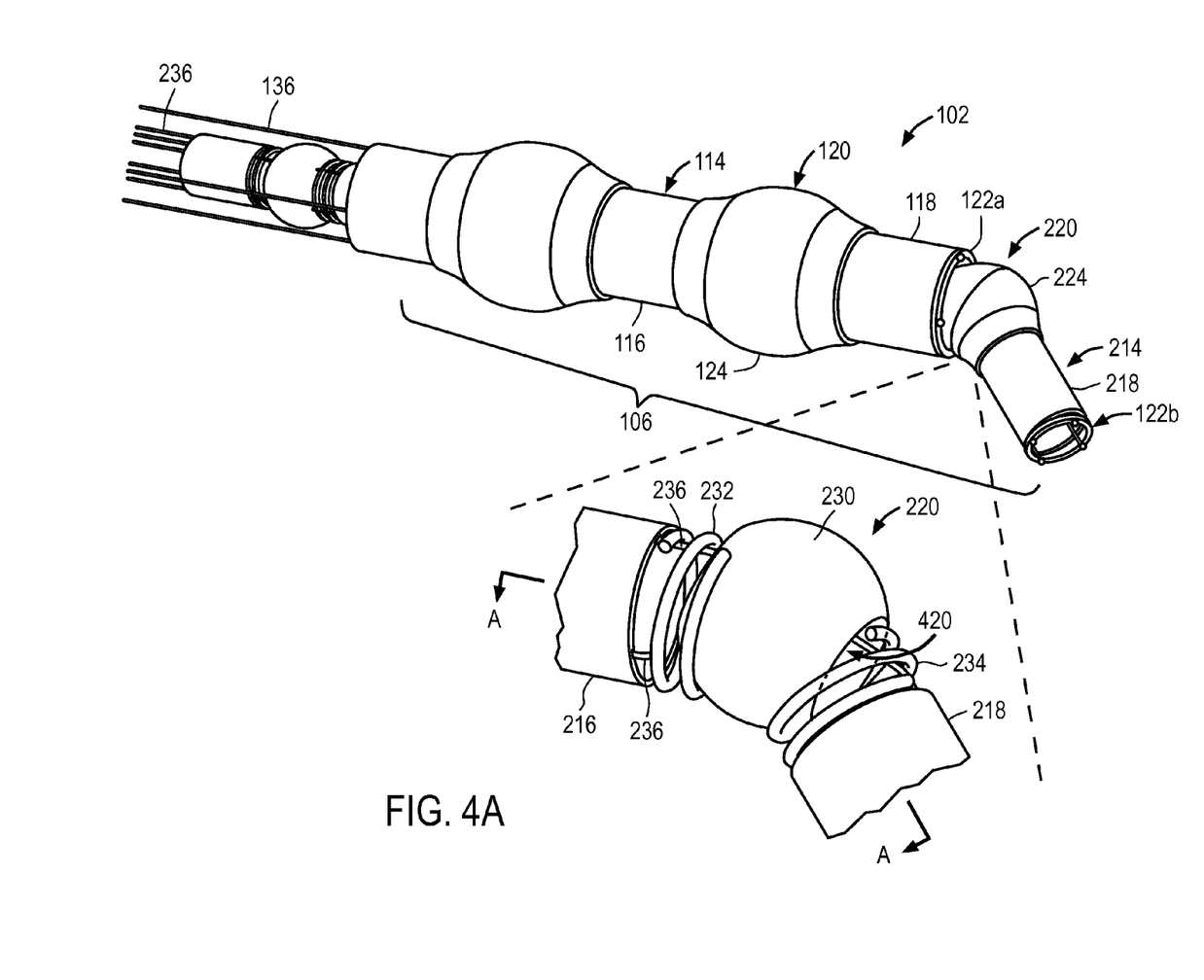
FIG. 4A illustrates a perspective view of a bending operation in progress of one embodiment of a modifiable elongated device.

Turning now to FIGS. 4A-4G, a bending operation of the elongated device is illustrated. In particular, it is important that during the bending operation the operator has precise control over the degree and direction of bend. Therefore in some embodiments, elongated body portion 102 is bent one tubular section at a time. Representatively, to bend a distal end of elongated body 102, inner articulated tube member 214 is advanced out the distal end of outer articulated tube member 114 as illustrated in FIG. 4A.

In some embodiments, one distal tubular section 218 and the associated joint member 220 are advanced beyond the end of outer articulated tube member 114. Inner articulated tube member 214 may be transitioned to the flexible or movable configuration by loosening control cables 236 prior to advancing it out the end of outer articulated tube member 114. Inner articulated tube member 114 may also be transitioned to the flexible configuration during or after advancing where outer articulated tube member 114 has a single radius of curvature. Once in the flexible or movable configuration, inner articulated tube member 214 can be bent or articulated about joint member 220 to the desired degree to form a bend.

Figure 4B:
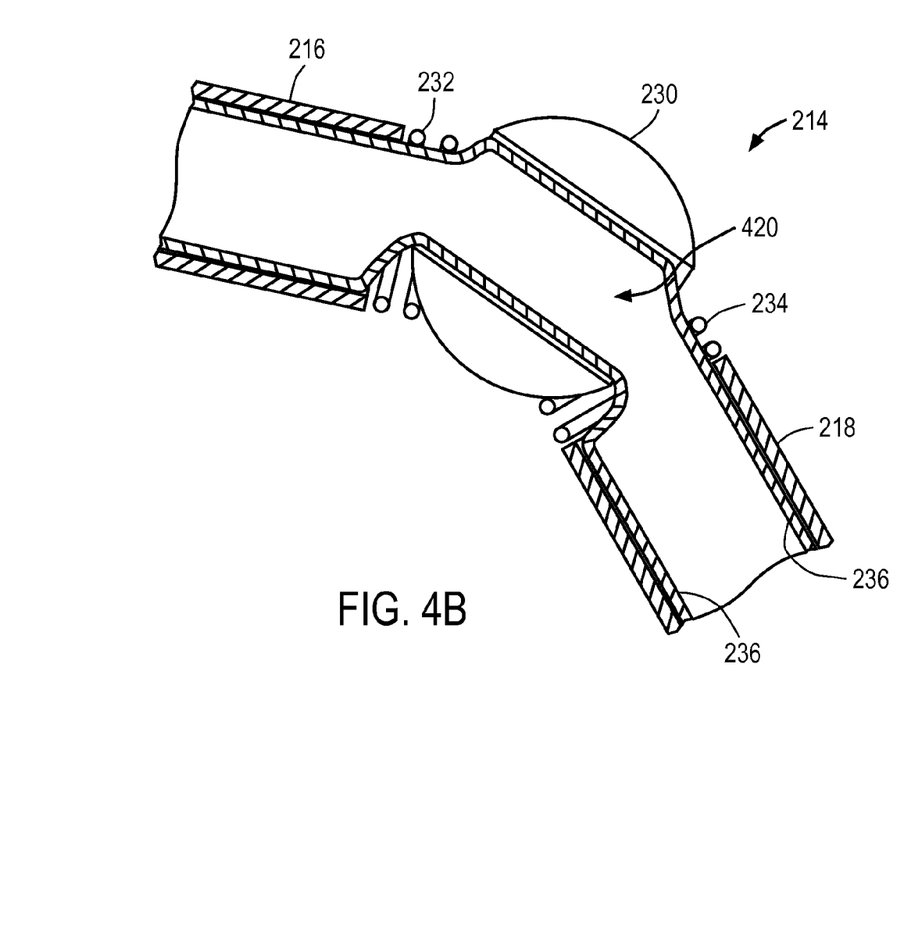
FIG. 4B illustrates a cross-sectional side view along line A-A' of FIG. 4A.

As can be seen from FIG. 4B, which is a cross-sectional view along line A-A' of FIG. 4A, ball joint 230 has a hollow pathway 420 formed through its center. In this aspect, control cables 236 can extend from the distal end to the proximal end of inner articulated tube member 214 within a continuous lumen formed within inner articulated tube member 214. Thus, although articulation about one joint member 220 is described, it is contemplated that control cables 236 extend through each of joint members 220 and may be used according to the above-described operation to articulate inner articulated tube member 214 about any of joint members 220.

As can be seen from the exploded view of joint member 220 in which cover member 224 is removed, pulling on one or more of cables 236 within the bend side causes spring member 232 and spring member 234 to pivot about the ball joint 230. Each tubular section may pivot or articulate about the associated joint member to a degree of, for example, from about 0 degrees to greater than 90 degrees, more specifically, from about 10 degrees to about 90 degrees, for example, from 20 degrees to 80 degrees, or from 30 degrees to about 70 degrees, or about 45 degrees.

Once the desired bend is achieved, tension on the associated control cables 236 is evenly increased, thereby increasing the friction in the ball joints so that inner articulated tube member 214 remains in the rigid or fixed configuration with the desired bend.

Figure 4C:
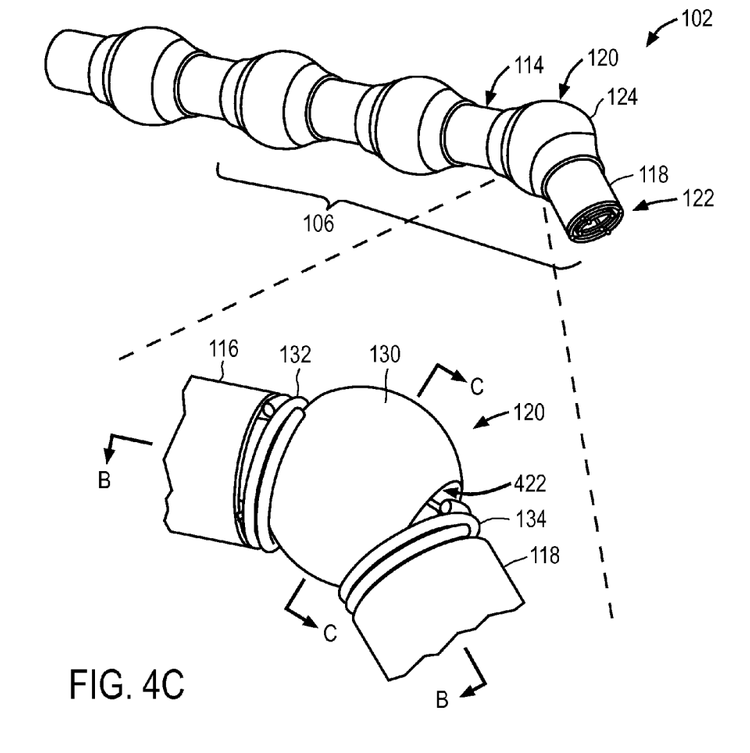
FIG. 4C illustrates a perspective view of a completed bending operation of one embodiment of a now fixed modifiable elongated device.

Next, outer articulated tube member 114 can be transitioned to the flexible or movable configuration, advanced over the bent distal end of inner articulate tube member 214 so that it also bends and then is transitioned to the fixed or rigid configuration as illustrated in FIG. 4C. In particular, when the flexible distal end of outer articulated tube member 114 is advanced over the bent inner articulated tube member 214, outer articulated tube member 114 articulates or bends to a substantially similar degree as inner articulated tube member 214. As can be seen from the exploded view of joint member 120, when outer articulated tube member 114 bends, spring member 132 and spring member 134 rotate about the ball 130. Tension on the associated cables 136 may be evenly increased to hold elongated body portion 102 in the bent shape.

Figures 4D, 4E:
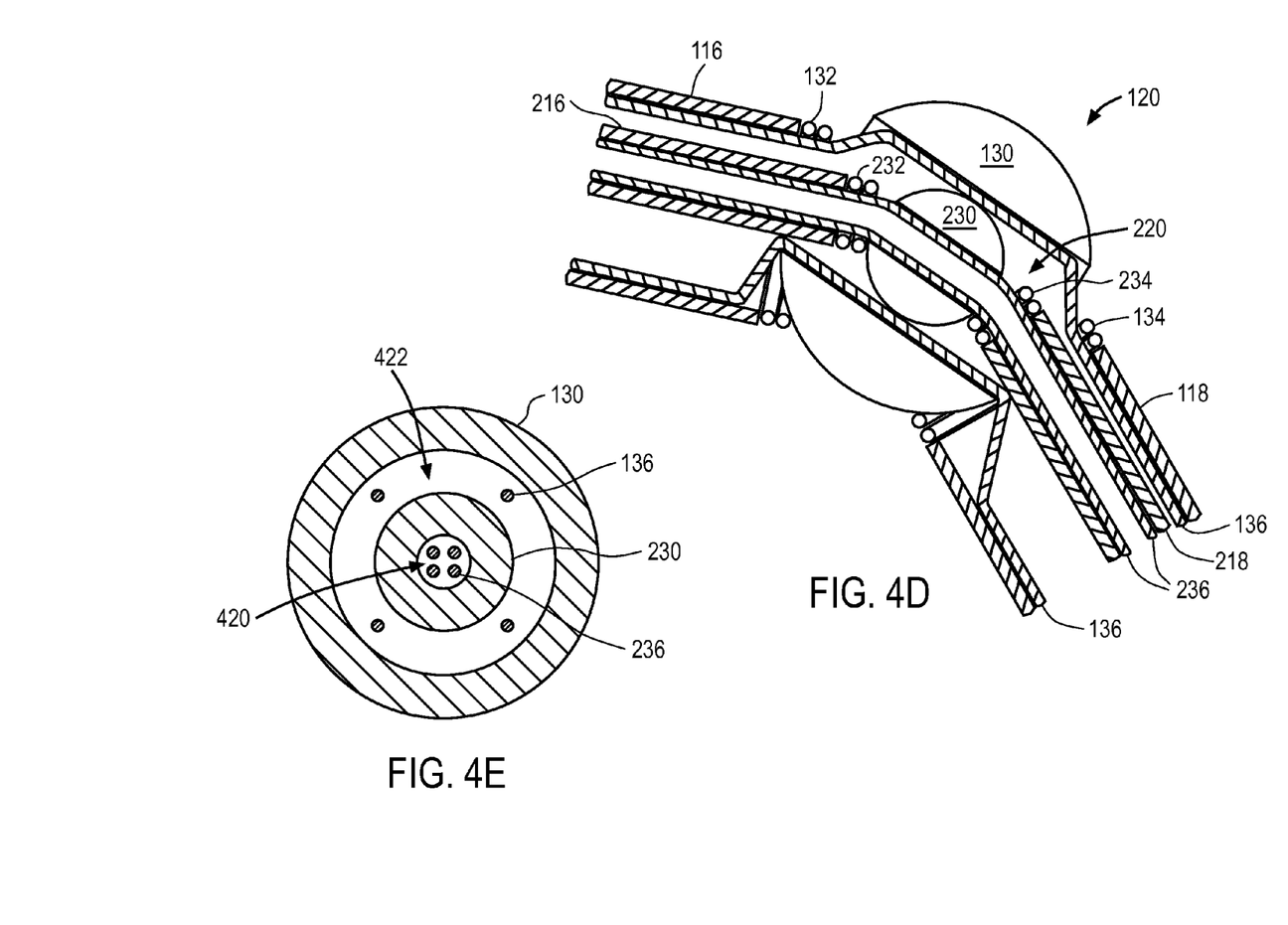
FIG. 4D illustrates a cross-sectional side view along line B-B' of FIG. 4C.
FIG. 4E illustrates a cross-sectional end view along line C-C' of FIG. 4C.

FIG. 4D, which is a cross-sectional view along lined B-B' of FIG. 4C, illustrates this operation in more detail. In particular, as can be seen from this view, outer articulated tube member 114 is advanced over the bent inner articulated tube member 214 previously discussed in reference to FIG. 4A. Similar to ball joint 230, ball joint 130 has a hollow pathway 422 formed therein so that a continuous lumen dimensioned to be advanced over inner articulated tube member 214 is formed between tubular sections 116, 118 and joint member 120. Ball joint 130 can be advanced over and substantially aligned with ball joint 230 of inner articulated tube member 214 so that outer articulated tube member 114 bends to a similar degree as inner articulated tube member 114.

Control cables 136 also pass through hollow pathway 422 along an outer surface of inner articulated tube member 214 so that they can be used to control the bending operation of tubular sections 116, 118. Although two control cables 136 are illustrated in FIG. 4D, it is to be understood that, outer articulated tube member 114 and inner articulated tube member 214 can include at least three control cables (in this embodiment, four control cables are arranged as shown in FIG. 4E). FIG. 4E illustrates a cross-sectional view along line C-C' of FIG. 4C. From this view, it can be seen that outer articulated tube member 114 can include four control cables 136 and inner articulated tube member 214 can also include four control cables 236. Control cables 236 extend through hollow pathway 420 of ball joint 230 of inner articulated tube member 214. Control cables 136 extend through hollow pathway 422 of ball joint 130 along an outer surface of ball joint 230. Control cables 136 and control cables 236 may be arranged in any manner within the respective ball joints 130, 230. Representatively, control cables 136 and control cables 236 may be evenly spaced or unevenly spaced with respect to one another. In some embodiments, ball joint 130 may include recesses or grooves formed along the wall of hollow pathway 422 that are dimensioned to receive and maintain a desired alignment of control cables 136 within ball joint 130. Ball joint 230 may include similar recesses or grooves to maintain and align control cables 236 within ball joint 230.

Figure 4F:
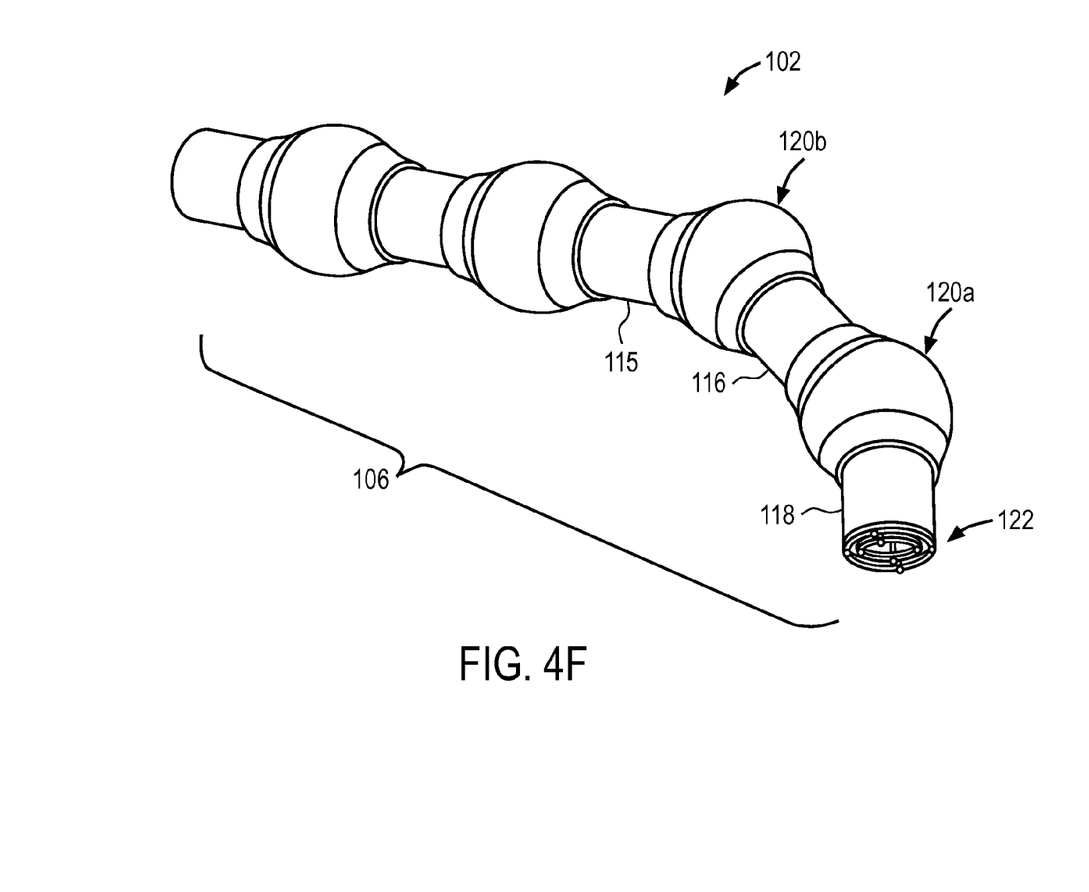
FIG. 4F illustrates a perspective view of a completed bending operation of one embodiment of a now fixed modifiable elongated device.
Figure 4G:
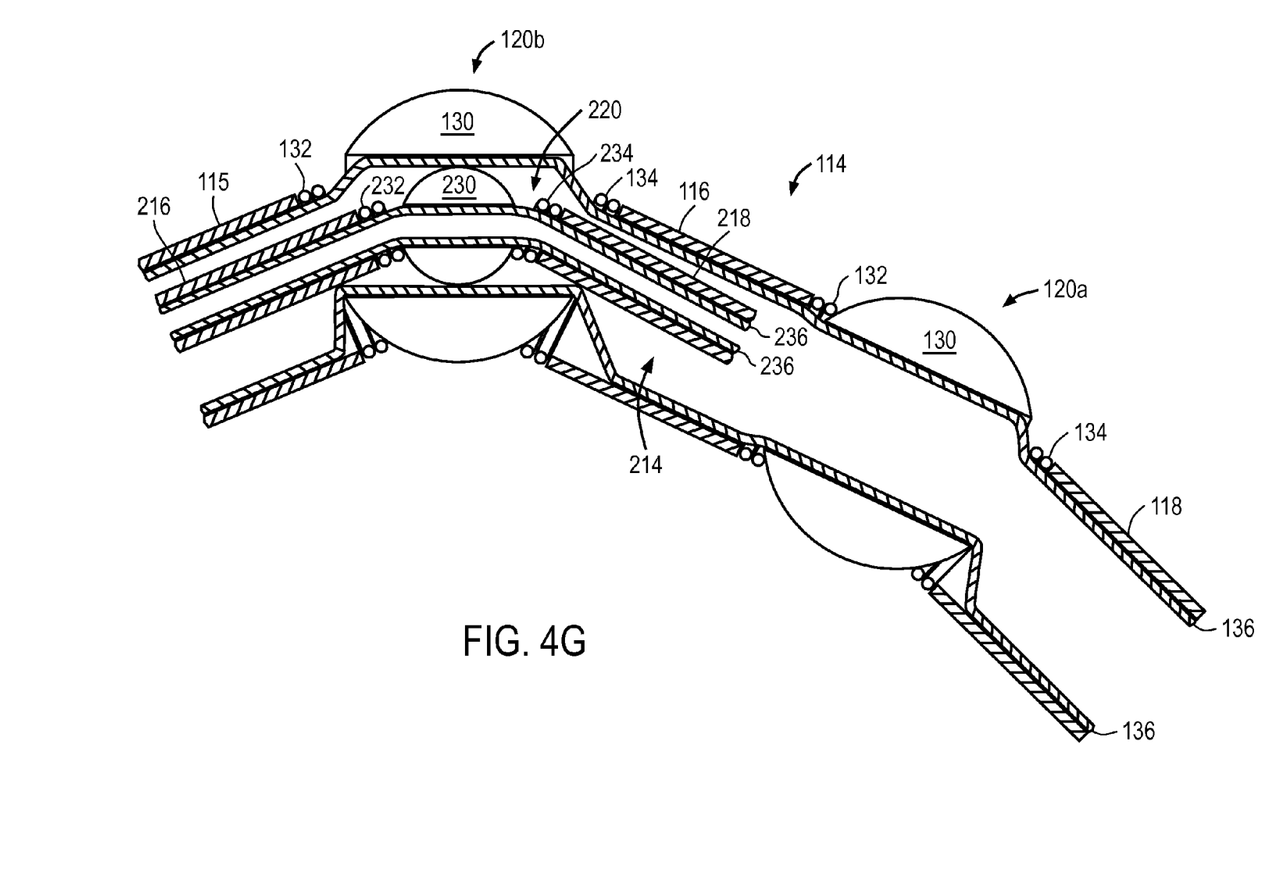
FIG. 4G illustrates a cross-sectional side view of FIG. 4F.

FIG. 4F illustrates a perspective view of outer articulated tube member having a second bend. FIG. 4G illustrates a cross-sectional side view of FIG. 4F. From FIG. 4G it can be seen that the bend of inner articulated tube member 214 previously described in reference to FIG. 4A is maintained. The bend may be maintained by tightening control cables 236 so that springs 232, 234 compress against ball joint 230 and hold inner articulated tube member in the fixed configuration. Control cables 136 of outer articulated tube member 114 are loosened so that outer articulated tube member 114 is in the flexible or modifiable configuration. Outer articulated tube member 114 is then advanced beyond the distal end of inner articulated tube member 214. In one embodiment, outer articulated tube member 114 is advanced so that distal joint member 120a and tubular section 118 are distal to inner articulated tube member 214. Proximal joint member 120b may be substantially aligned with joint member 220 of inner articulated tube member 214. Since outer articulated tube member 214 is in the flexible of modifiable configuration, tubular sections 115 and 116 on opposing sides of joint member 120b articulate with respect to ball joint 130 so that they form a bend similar to that of inner articulated tube member 214. Increasing a tension on one or more of control cables 136 causes distal tubular section 118 to articulate with respect to distal ball joint 130 of distal joint member 120a and form a second bend within the distal portion of outer articulated tube member 114. The bend formed by tubular sections 115, 116 on opposing sides of joint member 120b, however, remains the same since inner articulated tube member 214 is positioned within this portion of outer articulated tube member 114 in the fixed or rigid configuration.

This sequence of alternating advancing and bending of outer articulated tube member 114 and inner articulated tube member 214 can continue until the desired number of twists and turns of elongated body portion 102 are achieved.

The ability to change the curvature of elongated device 100 at multiple points along elongated body portion 102 provides several operational advantages. For example, in embodiments where elongated device 100 is a neuroendoscope, device 100 may be advanced into the brain at any point that is convenient and reach any other point by going around the major brain structures until the target region is reached. In addition, the device 100 is capable of backtracking to a previously passed region, for example to examine a blood vessel that may have been nicked by device 100 during the advancing, to examine the area and determine if it needs to be treated.

In addition, the ability to pivot or articulate one tubular section about the associated joint member at a time allows for gradual bending at multiple points along elongated body portion 102 so as to disturb as little brain tissue as possible. Representatively, in one embodiment, each tubular section is capable of articulating about the associated joint member within a range of from about 0 degrees to greater than 90 degrees, more specifically, from about 10 degrees to about 90 degrees, for example, from 20 degrees to 80 degrees, or from 30 degrees to about 70 degrees, or about 45 degrees.

In addition to facilitating bending of elongated device 100, the sliding of outer articulated tube member 114 and inner articulated tube member 214 with respect to one another allows for a length of device 100 to be changed. In particular, inner articulated tube member 214 may slide axially with respect to outer articulated tube member 214. In one embodiment, inner articulated tube member 214 is advanced a distance of one tubular section 218 and associated joint member 120 beyond the distal end of outer articulated tube member 114 to increase an overall length of device 100. Still further, outer articulated tube member 114 may be advanced a distance beyond the distal end of inner articulated tube member 214 to increase an overall length of device 100. The telescoping configuration of outer articulated tube member 114 and inner articulated tube member 214 allows for the overall length of device 100 to be increased or decreased as desired. In one embodiment, each tubular section may have a length of from about 3 millimeters to about 7 millimeters, for example, about 5 millimeters. Each joint member may have a similar overall length such that an overall length of elongated device 100 may be increased in increments of about 10 millimeters at a time. In other embodiments, any number of tubular sections maybe advanced beyond the distal end of the respective tube member 114 or 214 at a time and each tubular section may have any length sufficient to achieve the desired length and flexibility of elongated device 100.

For example, in embodiments where elongated device 100 is an endoscope, and more particularly a neuroendoscope, device 100 is initially advanced through the skull and into the brain toward the target region in a substantially straight, fixed configuration. It may, however, be desirable to view regions beyond the target region once device 100 is at the target region. To do so, distal tubular section 218 of inner articulated tube member 214 is advanced out the distal end of outer articulated tube member 114 just beyond joint member 220 (e.g., advanced approximately 10 millimeters). Tubular section 218 can remain extended or be retracted back into outer articulated tube member 114 as desired throughout the remainder of the procedure. It is noted that since it is desirable to disturb as little brain tissue as possible during the procedure, one tubular section 218 may be advanced out the distal end of outer articulated tube member 114 at a time so that the sections do not drop or sag. Alternatively, multiple tubular sections may be advanced out the distal end at one time.

As previously discussed, movement of the tubular sections about the associated joint members is controlled by modifying a tension on control cables 136, 236 using control member 108. Control cables 136, 236 are attached at their respective distal ends to guide member 122. Guide member 122 may include an outer guide member 122A attached to control cables 136 and a separate inner guide member 122B attached to control cables 236. Outer guide member 122A helps to control outer articulated tube member 114 and inner guide member 122B helps to control inner articulated tube member 214.

Figure 5:
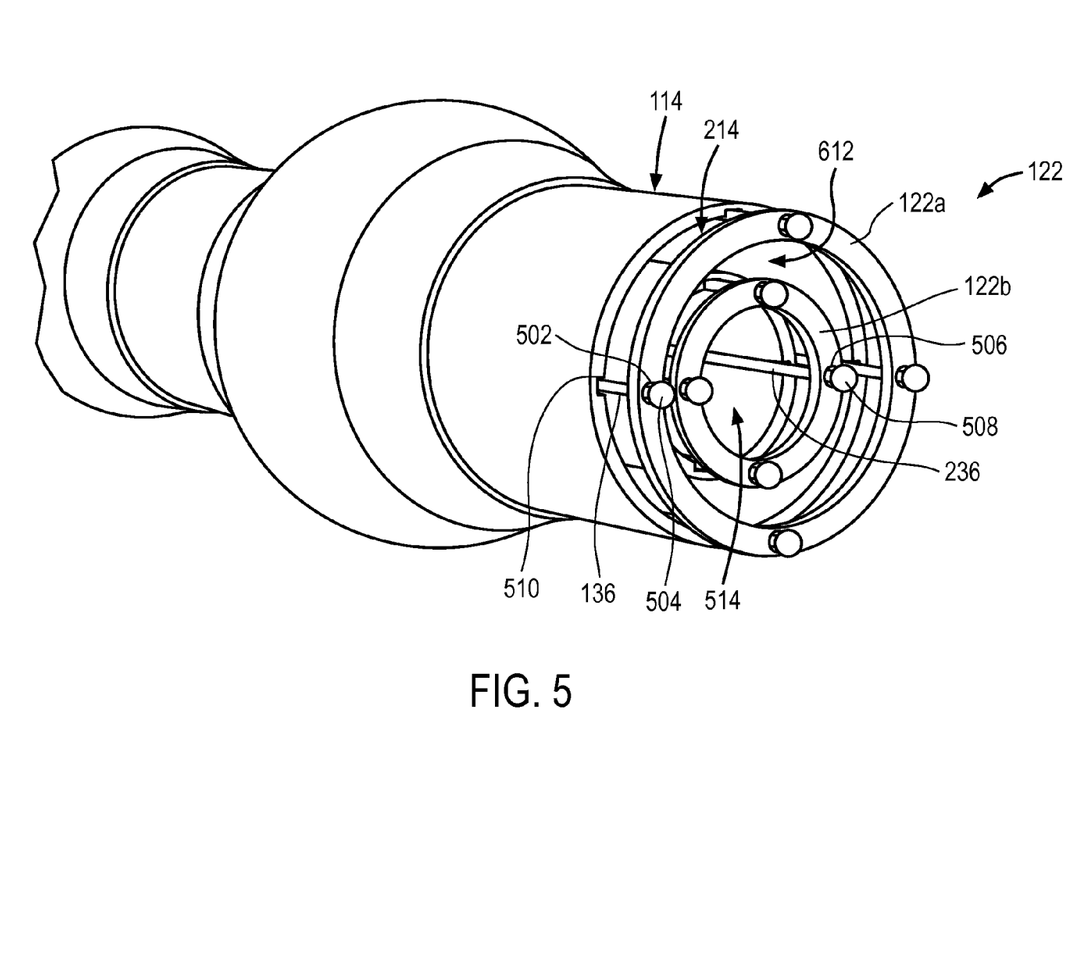
FIG. 5 illustrates a perspective view of one embodiment of a guide member.

FIG. 5 illustrates a perspective view of one embodiment of a guide member. In one embodiment, outer guide member 122A and inner guide member 122B are ring shaped structures, with inner guide member 122B being positioned concentrically inward from outer guide member 122A. In one embodiment, outer guide member 122A and inner guide member 122B are slidably attached to the ends of control cables 136, 236, respectively, so that they can "float" over the distal end of elongated device 100. Representatively, each of control cables 136 may be attached at points around a circumference of outer guide member 122A by inserting the end of control cables 136 through respective holes 502 within outer guide member 122A. Plug members 504 that are larger than holes 502 may then be secured at the end of each of control cables 136 extending through holes 502. Similarly, each of control cables 236 may be attached around a circumference of inner guide member 122B by inserting the end of control cables 236 through respective holes 506 within inner guide member 122B and securing plug members 508 at the end of each of control cables 236. Plug members 504, 508, may be, for example, ball shaped structures made of any material such as a metal, polymer or the like. In the case of a metal, plug members 504, 508 may be soldered to the end of control cables 136, 236, respectively.

Control cables 136, 236 may be evenly spaced around the circumference of outer guide member 122A and inner guide member 122B, respectively. Alternatively, a spacing of control cables 136, 236 about outer guide member 122A and inner guide member 122B, respectively, may be unevenly spaced. When control cables 136, 236 are in a resting position, in other words tension is not being applied to them to turn or tighten elongated device 100, guide members 122A and 122B can be spaced a distance from the distal end of outer articulated tube member 114 and inner articulated tube member 214, respectively, as illustrated in FIG. 5. Alternatively, guide members 122A and 122B can rest on the distal end of outer articulated tube member 114 and inner articulated tube member 214, respectively, until tension is applied to control cables 136, 236. Once tension is applied to control cable 136 or control cable 236, the respective guide member is pulled toward and presses on the distal end of the outer articulated tube member 114 or inner articulated tube member 214 to facilitate bending or tightening of the tubular sections about the associated joint members.

Floating outer guide member 122A and inner guide member 122B over the distal ends of outer articulated tube member 114 and inner articulated tube member 214, respectively, allows for optimal control of elongated device 100 during operation. In particular, the "floating" nature of guide members 122A and 122B allows for the application of asymmetrical forces for bending of outer articulated tube member 114 and inner articulated tube member 116, respectively, and symmetrical forces for making members 114, 116 rigid once bent. As previously discussed, device 100 is capable of bending in several different directions as illustrated in FIG. 3. Pulling on one or more of control cables 136 and/or control cables 236 pulls outer guide member 122A and inner guide member 122B against the distal end of outer articulated tube member 114 and inner articulated tube member 214, respectively. Outer guide member 122A and inner guide member 122B in turn, apply a force to the distal end of outer articulated tube member 114 and inner articulated tube member 214 which can be used to bend elongated device 100 in a desired direction. Since outer guide member 122A and inner guide member 122B are circular and contact an entire circumference of the associated articulated tube member 114, 214, the force applied by the associated control cables at points around guide members 122A, 122B can be distributed to various points around outer articulated tube member 114 and inner articulated tube member 214, not just at the points where control cables 136, 236 are attached. In this aspect, guide members 122A, 122B provide a more analog way of delivering force applied by control cables 136, 236 along outer articulated tube member 114 and inner articulated tube member 214.

Alternatively, the ends of control cables 136, 236 may be fixed directly to outer guide member 122A and inner guide member 122B, respectively.

Each of guide members 122A, 122B may be made of any material and of any dimensions suitable for transferring a force from control cables 136, 236, respectively, along outer articulated tube member 114 and inner articulated tube member 214 as previously discussed. Representatively, guide members 122A, 122B may be made of, for example, a metal material such as titanium. Guide members 122A, 122B may have a thickness sufficient to transfer the force from control cables 136, 236 to outer articulated tube member 114 and inner articulated tube member 214 without bending.

Figure 6:
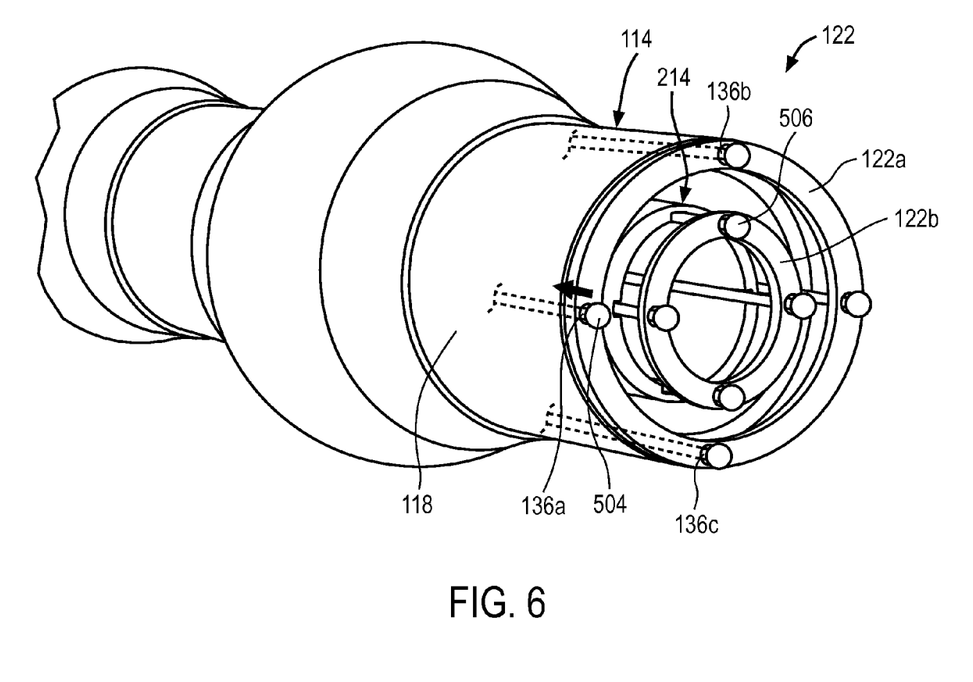
FIG. 6 illustrates a perspective view of one embodiment of a guide member during a bending operation of a modifiable elongated device.

As previously discussed, control cables 136, 236 extend from a proximal end to a distal end of elongated device 100. Control cables 136, 236 may extend along the inner surface of outer articulated tube member 114 and inner articulated tube member 214, respectively. In this aspect, channel 612 may be provided between an outer surface of inner articulated tube member 214 and an inner surface of outer articulated tube member 114 to accommodate control cables 136. Channel 612 may be an annular channel that extends from the proximal to the distal end of elongated body portion 102. In addition, channel 612 may be dimensioned to accommodate other instruments the user may want to advance along the length of elongated device 100 and out the distal end to the target region. For example, in the case of an endoscope, channel 612 may accommodate one or more of an operating instrument, light source or camera. Representatively, in some embodiments, the instrument and light source are positioned between the inner articulated tube member 214 and the outer articulated tube member 114 and the camera is positioned within lumen 514 provided within the inner articulated tube member 114.

Grooves or recesses 510 can be formed along an inner surface of the tubular sections of outer articulated tube member 114 to maintain alignment of control cables 136, or other devices, positioned within outer articulated tube member 114. Similarly, a groove or recess may be formed along an inner surface of inner articulated tube member 214 to receive control cables 236, or other devices positioned within inner articulated tube member 214.

Returning to the operation of guide member 122, FIG. 6 illustrates the orientation of guide member 122 when control cables 136, 236 are pulled to bend elongated device 100. For example control cable 136A is shown pulled in a direction toward the proximal end of device 100. This in turn, pulls a side of outer guide member 122A connected to control cable 136A against the distal end of outer articulated tube member 114 and causes tubular sections of outer articulated tube member 114 to pivot or articulate with respect to their associated joint member in the direction of the force being applied along control cable 136A. Inner articulated tube member 214 may be in the movable or flexible configuration such that it bends along with outer articulated tube member 114. Alternatively, one or more of control cables 236 may also be pulled to independently bend inner articulated tube member 214 in the desired direction. In the illustrated embodiment, however, tension is not applied to control cables 236 so that guide member 122B is seen spaced a distance from the distal end of inner articulated tube member 214.

Elongated device 100 may be bent in other directions by pulling on any one or more of the remaining control cables 136, 236. For example, when the user pulls on only 136A, the side of elongated device 100 along control cable 136A contracts and bends. Similarly, pulling on, for example, control cable 136B or control cable 136A contracts and bends the side of elongated device 100 along the associated cable. Other areas of device 100 between each of control cables 136, e.g., cables 136A, 136B and 136c (the fourth control cable cannot be seen from this view), can also contract and bend by pulling on two or more cables at a time. For example, pulling on control cables 136A and 136B pulls the portion of guide member 122A between control cables 136A and 136B against an area of the distal end of outer articulated tube member 114 between the cables causing elongated device to contract and bend along the side between the cables. Thus, elongated device 100 is cable of bending in a variety of different directions.

Figure 7:
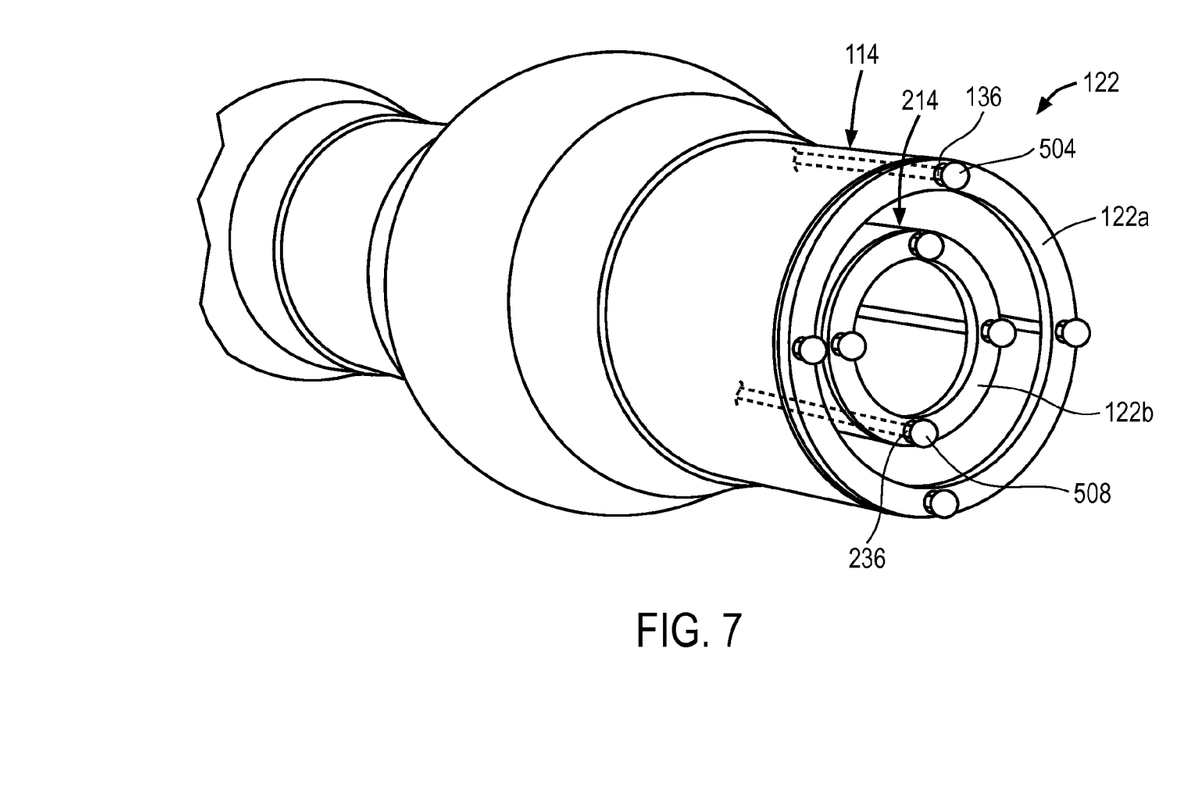
FIG. 7 illustrates a perspective view of one embodiment of a guide member when a modifiable elongated device is in a fixed or rigid configuration.

FIG. 7 illustrates a perspective view of one embodiment of the guide member of FIG. 1. In this embodiment, the positioning of guide member 122A and guide member is shown when tension is applied to all of control cables 136, 236. In particular, when each of control cables 136 are pulled in a proximal direction, for example to maintain elongated device 100 in the rigid or fixed configuration, guide member 122A of outer articulated tube member 114 is pulled against the distal end of outer articulated tube member 114 as shown. Similarly, when each of control cables 236 are pulled in the proximal direction, guide member 122B presses against the distal end of inner articulated tube member 214 to tighten the associated tubular sections against the joint members. When tension on control cables 136 and control cables 236 is released, guide members 122A, 122B may remain resting along the distal end of the associated articulated tube member or space themselves a distance from the distal end.

In the preceding detailed description, specific embodiments are described. It will, however, be evident that various modifications and changes may be made thereto without departing from the broader spirit and scope of the claims. For example, the relative dimensions of the components of the elongated device are scalable so that the elongated device is suitable for use in a variety of different fields that could benefit from an elongated device capable of transitioning between a modifiable and fixed configuration as well as having a modifiable length. Some representative fields include surgery and medicine, repair and maintenance, robotics, avionics, aerospace engineering, civil engineering, surveillance and discrete photography, architecture and military. More specifically, the elongated device could be used for pre-visualization of scale models of proposed buildings and cities (architectural endoscopy), internal inspection of complex technical systems (borescope), examination of improvised explosive devices by bomb disposal personnel and for conducting surveillance via tight spaces. In this aspect, although the elongated device is described as being capable of accommodating instruments such as surgical instruments, cameras and light sources, other instruments may also be advanced or positioned within the elongated device depending upon the desired use. The specification and drawings are, accordingly, to be regarded in an illustrative rather than restrictive sense.

What is claimed is:

1. An apparatus comprising:
    an outer articulated tube member having a distal portion and a proximal portion, the distal portion of the outer articulated tube member having a first tubular section and a second tubular section connected together by an outer joint member; and
    an inner articulated tube member having a distal portion and a proximal portion positioned within the outer articulated tube member, the distal portion of the inner articulated tube member having a first tubular section and a second tubular section connected together by an inner joint member, and
    wherein the first tubular section and the second tubular section of each of the outer articulated tube member and the inner articulated tube member pivot about the outer joint member and the inner joint member, respectively, to any position within a volume of a cone in a first configuration and are fixed with respect to one another in a second configuration, and
    wherein at least one of the outer joint member and the inner joint member comprises a spring and ball joint between the first tubular section and the second tubular section, the spring and ball joint having a first spring positioned between an end of the first tubular section and a ball, and a second spring positioned between an end of the second tubular section and the ball such that both the first tubular section and the second tubular section move around the ball.

2. The apparatus of claim 1 wherein the apparatus is a neuroendoscope and the outer articulated tube member is dimensioned for insertion within a body.

3. The apparatus of claim 1 wherein the first tubular section and the second tubular section of the inner articulated tube member are in the first configuration and the first tubular section and second tubular section of the outer articulated tube member are in the second configuration.

4. The apparatus of claim 1 wherein the first tubular section of the outer articulated tube member defines a distal end and the inner articulated tube member is movable in an axial direction within the outer articulated tube member such that the first tubular section of the inner articulated tube member is capable of advancing beyond the distal end of the outer articulated tube member.

5. The apparatus of claim 4 wherein the first tubular section and the second tubular section of the inner articulated tube member are modifiable between the first configuration and the second configuration when the first tubular section is advanced beyond the distal end of the outer articulated tube member.

6. The apparatus of claim 1 further comprising:
    at least one control cable coupled to the first tubular section and the second tubular section of at least one of the outer articulated tube member and the inner articulated tube member to control the first tubular section and the second tubular section in the first configuration and the second configuration.

7. The apparatus of claim 1 further comprising:
    a guide member positioned distal to the first tubular section of at least one of the inner articulated tube member and the outer articulated tube member, wherein the guide member is movably attached to the first tubular section by a control cable terminating at the guide member and extending axially along the first tubular section.

8. The apparatus of claim 1 wherein a channel is formed between the inner articulated tube member and the outer articulated tube member, the channel dimensioned to receive an instrument used for performing a procedure within the body.

9. An endoscope comprising:
    an outer tube member dimensioned for insertion within a body;
    an inner tube member positioned within the outer tube member; and
    a guide member positioned at a distal end of at least one of the outer tube member and the inner tube member, wherein the guide member comprises a ring having substantially the same diameter as the at least one of the outer tube member and the inner tube member and movably attached to at least one of the outer tube member and the inner tube member by a control cable terminating at the guide member and extending from the distal end to a proximal end of at least one of the outer tube member and the inner tube member such that at least one of the outer tube member and the inner tube member is modifiable between a first fixed configuration and a second movable configuration while within the body, and
    wherein at least one of the outer tube member and the inner tube member comprise a first tubular section and a second tubular section connected together by a spring and ball joint, the spring and ball joint having a first spring positioned between an end of the first tubular section and a ball, and a second spring positioned between an end of the second tubular section and the ball such that both the first tubular section and the second tubular section move around the ball.

10. The endoscope of claim 9 wherein the inner tube member is capable of telescoping with respect to the outer tube member to increase a length of the endoscope.

11. The endoscope of claim 9 wherein the first tubular section and the second tubular section are fixed with respect to one another in the first fixed configuration and movable with respect to one another in the second movable configuration.

12. The endoscope of claim 9 further comprising:
    at least one control cable between a distal end and a proximal end of at least one of the outer tube member and the inner tube member to control the outer tube member or the inner tube member in the first fixed configuration and the second movable configuration.

13. The endoscope of claim 9 wherein a channel is formed between the outer tube member and the inner tube member, the channel dimensioned to receive an instrument used for performing a procedure within the body.

* * * * *